United States Patent [19]

Stahl

[11] 4,236,895
[45] Dec. 2, 1980

[54] ANALYTICAL APPARATUS AND METHOD EMPLOYING PURIFIED OZONE

[75] Inventor: Quade R. Stahl, Springfield, Va.

[73] Assignee: Meloy Laboratories, Inc., Springfield, Va.

[21] Appl. No.: 47,570

[22] Filed: Jun. 11, 1979

[51] Int. Cl.³ .............................................. G01N 21/76
[52] U.S. Cl. ............................... 23/232 R; 23/232 E; 422/52
[58] Field of Search ........... 422/52; 23/230 R, 232 R, 23/232 E

[56] References Cited

U.S. PATENT DOCUMENTS

| 511,330 | 12/1893 | Fahrig . | |
|---|---|---|---|
| 994,294 | 6/1911 | Woillard . | |
| 2,872,397 | 2/1959 | Kiffer . | |
| 3,579,305 | 5/1971 | Neti . | |
| 3,967,933 | 7/1976 | Etess et al. | 422/52 |
| 4,018,562 | 4/1977 | Parks et al. | 422/52 |
| 4,077,774 | 3/1978 | Neti et al. | 422/52 |

OTHER PUBLICATIONS

Ogden, "Ozonation Today", *Industry Water Engineering*, Jun. 1970.

*Primary Examiner*—R. E. Serwin
*Attorney, Agent, or Firm*—Shapiro and Shapiro

[57] ABSTRACT

Ozone generated for chemiluminescent reaction in an analyzer for the measurement of oxides of nitrogen, for example, is purified by passing the ozone through a bed of silica gel, thereby removing substances that interfere with the analysis.

13 Claims, 1 Drawing Figure

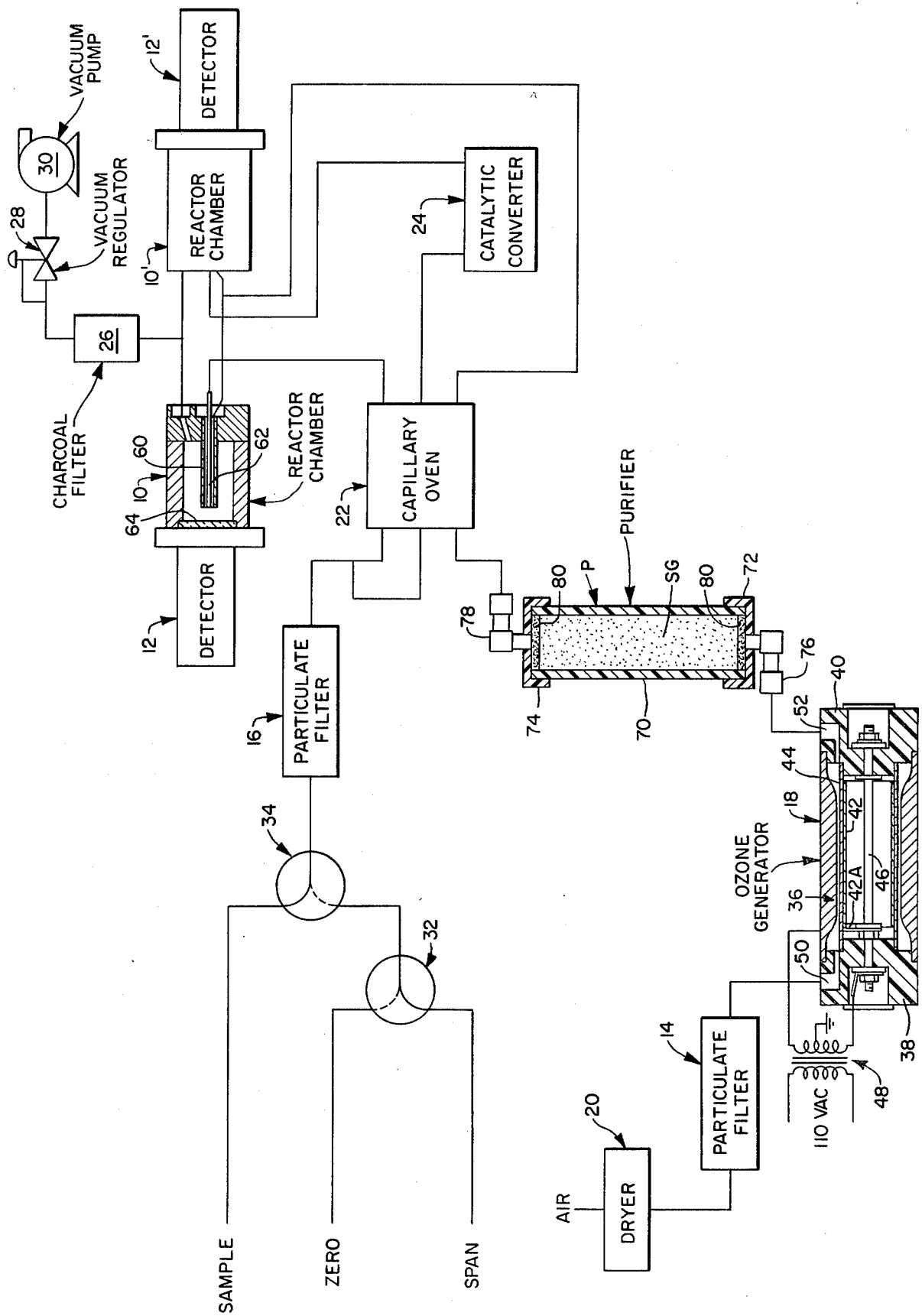

ANALYTICAL APPARATUS AND METHOD EMPLOYING PURIFIED OZONE

BACKGROUND OF THE INVENTION

This invention relates to analysis employing ozone as a reactant and is especially concerned with improvements in nitrogen oxides analyzers in which ozone is generated for chemiluminescent reactions.

One type of nitrogen oxides analyzer now in wide use employs the chemiluminescent reaction of nitric oxide (NO) and ozone ($O_3$). The ozone can be produced from ambient air by means of an electric discharge type ozone generator. The reaction between the ozone and the nitric oxide in a sample occurs in a reactor chamber having a transmissive window through which light produced by the chemiluminescent reaction is transmitted to a detector, commonly a photomultiplier tube (PMT). Several problems in such analyzers have been observed, namely, higher than normal zero based output, erratic response to sample or span gases, particularly during winter periods, and the need for frequent maintenance to keep the reactor chamber clean and to replace parts that have deteriorated. Although these deficiencies have been known for some time, the reasons for the problems have not been known, and the problems have resisted practical solution.

BRIEF DESCRIPTION OF THE INVENTION

Underlying the present invention is the discovery that the foregoing problems in nitrogen oxides analyzers of the type described stem from a single, common source—impurities in the ozone supplied to the reactor chambers.

More specifically, it has been discovered that when ozone is generated as alluded to earlier, impurities are produced that interfere with the desired chemiluminescent analysis. The amounts and types of impurity species appear to be somewhat dependent upon the dryness of the air supplied to the ozone generator, the flow rate of the air through the generator, the frequency and voltage of the generator, and the presence of hydrocarbons, nitrogen oxides and other compounds in the air. The impurities, and/or by-products from reactions of the impurities with sample air, produce spurious light in the reactor chamber and produce deposits that coat the window of the reactor chamber and block the desired light from the chemiluminescent reaction of nitric oxide and ozone. Moreover, the impurities and their by-products appear to be highly reactive, strongly acid species which attack material such as epoxy, O-rings, and metals used in the pneumatic system of the analyzer.

Accordingly, it is a principal object of the invention to provide improved apparatus and methods such as those employed in the measurement of nitrogen oxides by chemiluminescent reactions involving ozone.

A further object of the invention is to provide improved apparatus and methods employing ozone in chemiluminescent reactions and in which impurities produced in ozone generation and the effects of such impurities are eliminated.

Briefly stated, in one of its broader aspects, the invention employs a purifier in the flow path between an ozone generator and an analytical instrument employing ozone in a chemiluminescent reaction. More particularly, the invention employs silica gel to remove impurities from the output stream of an ozone generator.

BRIEF DESCRIPTION OF THE DRAWING

The invention will be further described in conjunction with the accompanying drawing, the single FIGURE of which is a flow diagram illustrating a typical analyzer employing the invention, certain parts of the FIGURE being shown in cross-section.

DETAILED DESCRIPTION OF THE PREFERRED EMBODIMENT

The invention will be described with reference to its use in a nitrogen oxides analyzer, although the invention has broader applicability. The drawing illustrates a representative nitrogen oxides analyzer that performs continuous dry analysis of nitric oxide (NO), nitrogen dioxide ($NO_2$) and total oxides of nitrogen ($NO_x$, NO, and $NO_2$) in gas mixtures. The analyzer utilizes the highly sensitive chemiluminescent reaction between NO and $O_3$, which produces high energy excited $NO_2^*$ molecules. When $NO_2^*$ molecules revert to a lower energy state, they produce light in the near infrared region (0.6 to 3.0 microns). This operation is summarized in the following equations:

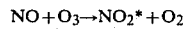

$$NO + O_3 \rightarrow NO_2^* + O_2$$

$$NO_2^* \rightarrow NO_2 + \text{light}.$$

The intensity of the light produced is directly proportional to the NO concentration.

Principal parts of a commercial analyzer to which the invention may be applied are illustrated in the drawing and include a pair of reactor chambers 10, 10' with associated detectors 12, 12', particulate filters 14, 16, an ozone generator 18, a dryer 20, a capillary oven 22, a catalytic converter 24, a charcoal filter 26, a vacuum regulator 28, a vacuum pump 30, and solenoid valves 32 and 34. A purifier P is added to the analyzer in accordance with the present invention.

Neglecting the purifier for the moment, the analyzer shown may be further described as follows. Ambient air is dried by the dryer 20 (which may be a conventional type including calcium sulfate or silica gel, for example) to a relative humidity preferably less than 40%. The dried air passes through particulate filter 14 to ozone generator 18, which, in the form shown, is an electric discharge type producing ozone by Corona discharge between a pair of electrodes. One of the electrodes may be a stainless steel tubular housing 36 provided with PVC end caps 38 and 40 sealed to the housing by O-rings, for example. The other electrode may be an aluminum foil tape 42 adhesively adhered to the inner surface of a glass cylinder 44 also sealed to end caps 38 and 40, as by O-rings. A steel rod 46 extends between and ties together the end caps and is electrically connected to an end portion 42A of the foil electrode. An electric potential of, for example, 5500 volts AC is applied across the electrodes from the secondary winding of a transformer 48, the center tap of which may be grounded. 110 volts 60 Hz AC may be applied to the primary winding of the transformer. The ambient air, at a flow rate of 100–300 cc/min, for example, enters an inlet passage 50 in end cap 38, passes between the glass cylinder 44 and the housing 36 (being distributed around the circumference of these elements) and exits through an outlet passage 52 in end cap 40, some of the oxygen in the air stream being converted to ozone (for example, 1000–7000 parts per million) by the electric discharge between the electrodes. The output stream of the ozone generator flows through the capillary oven 22. The oven is employed to provide temperature-controlled capillary restrictors to stabilize the flow of ozone (and other gases) into the reactor chambers.

In the illustrative analyzer there are three gas inlet ports designated "Sample" ... "Zero" ... and "Span." In the "sample" or normal operation mode, the instrument simultaneously analyzes the NO and $NO_x$ in the sample. Sample air enters the Sample port, passes through solenoid valve 34, particulate filter 16, a temperature-controlled capillary in oven 22 and into the reactor chamber 10. The sample air also passes through another temperature-controlled capillary in oven 22, and then through the catalytic converter 24 (which converts $NO_2$ to NO) and into the reactor chamber 10'. In the "zero" mode, pure air enters through the Zero port, passes through valves 32 and 34 (now switched to their alternate position) and continues into the reactor chambers as before. When the analyzer is in the "span" mode, air enters through the Span port and passes through valves 32 and 34 (only valve 34 is switched), continuing along the same path as in the zero mode.

The structure and operation of the reactor chambers may be identical. Only chamber 10 is shown in some detail. As illustrated, the ozone and the sample enter the chamber through coaxial tubing 60, 62, respectively. Where the tubes meet at their outlets, the chemiluminescent reaction occurs, and light from the reaction passes through a quartz window 64 to the detector 12. The exhaust gas passes from chamber 10 through charcoal filter 26, the vacuum regulator 28 and the vacuum pump 30.

The following additional information concerning the illustrative analyzer may be of interest. An optical filter is normally employed between each reactor chamber and its detector to provide desired selectivity, and a light chopper is normally employed between the filter and the detector to chop the light received by the detector. All gas sampling lines to the reactor chambers may be Teflon tubing with stainless steel connectors, and the exhaust tubing leading to the charcoal filter may also be Teflon tubing. The activated charcoal filter reduces the excess ozone and removes $NO_2$ from the reactor exhaust gas. The particulate filters may include sintered stainless steel filter elements. The vacuum pump may be a dual-head type which draws air through the ozone, span, and sample lines and provides the required pressure in the reactor chambers. The vacuum regulator may maintain both reactor chamber pressures at 160 torr, for example. The electronics conventionally employed in analyzers of the type shown are well known.

In the operation of the analyzer just described, in the sample mode sample air and ozone are introduced into the reactor chambers, where they efficiently mix and chemically react to produce light energy. The light energy passes through the selective filters and light choppers to the detectors, which measure the intensity of the chemiluminescent radiation. The light choppers produce pulsed DC outputs from the detectors, the amplitude of which is proportional to the light intensity. Subsequently, a signal amplifier and demodulator convert the pulsed waves to DC analog signals.

The output produced from the reactor chamber 10 measures the concentration of NO in the sample. The output from reactor chamber 10' measures $NO_x$, the catalytic converter converting the $NO_2$ molecules to NO molecules for reaction with the ozone. $NO_2$ concentration may be obtained by electronically substracting the output of detector 12 from the output of detector 12'.

As stated earlier, it has been discovered, in accordance with the invention, that impurities in the ozone produced by ozone generator 18 are responsible for faulty performance and maintenance problems in analyzers of the type just described. Yellow-red, oily-crystal deposits in the pneumatic system, particularly the reaction chambers, have been observed, and it has been discovered that most of these deposits are impurities and/or by-products of impurities produced by the ozone generator 18. Such impurities and by-products produce spurious light that is detected by the detectors 12 and 12', produce deposits on the windows of the reactor chambers that block desired light, and attack materials of the pneumatic system.

In accordance with the invention, it has been further discovered that the foregoing problems may be solved by providing a purifier P for purifying the output stream of the ozone generator 18, so that the impurities and their effects are eliminated. The purifier must eliminate the impurities without eliminating significant ozone and must be stable with high concentrations of ozone. As a practical matter, the purifier must employ a purifying material that has long life (e.g., at least 6 months to a year), that is relatively inexpensive, and that is readily available. Silica gel has been found to meet all of these requirements.

Silica gel is a precipitated silicic acid in the form of lustrous granules and is available from many commerical sources. For example, type GCA-004 Anasorb silica gel, 100/110 mesh available from Analabs has been found suitable. As shown, the silica gel may be held in a tubular housing, which may comprise a PVC cylinder 70 with PVC end caps 72 and 74 attached thereto by an epoxy resin adhesive. The end caps have bores with associated inlet and outlet fittings 76 and 78. Wads of glass wool 80 may be provided at opposite ends of the housing to retain a bed of silica gel particles SG which fills the space between the glass wool wads (but need not be tightly packed into the housing). Typically, the purifier housing may be about 4 inches long with an inner diameter of about $\frac{1}{2}$ inch and may contain approximately 0.8 cubic inch of 100/110 mesh silica gel particles. Normally, the purifier operates at room temperature at atmospheric or near atmospheric pressure, but its operation is not limited to such conditions.

By virtue of the invention, the previously described spurious or erratic performance of the analyzer is eliminated, and much less maintenance is required. Red-yellow colored deposits on the silica gel are noted, as well as the absence of such deposits in the reactor chambers. Satisfactory analyzer performance has been demonstrated in tests over protracted periods, and the presence of the purifier has not detracted from the desired ozone-saturated mode of reactor chamber operation (saturation being apparent from the fact that test results are not affected by temperature variations). A further advantage of the invention is that the relative humidity of the air introduced into the ozone generator need not be as low as has been required previously. Merely by way of example, the invention may be employed in the Model NA520 and NA530 Nitrogen Oxides Analyzers manufactured and sold by Meloy Laboratories, Inc., the assignee of the present invention.

While a preferred embodiment of the invention has been shown and described, it will be apparent to those skilled in the art that changes can be made in this embodiment without departing from the principles and spirit of the invention, the scope of which is defined in the appended claims.

I claim:

1. In analytical apparatus having an ozone generator and a reactor chamber in which generated ozone is employed in a chemiluminescent reaction, purifier means connected between the output of the ozone generator and the ozone input to the reactor chamber for removing impurities from the generated ozone.

2. Apparatus in accordance with claim 1, wherein the purifier means comprises silica gel.

3. Apparatus in accordance with claim 2, wherein the silica gel is in the form of a bed of particles through which the output of the ozone generator is passed.

4. Apparatus in accordance with claim 1, wherein the ozone generator is of the type employing an electric discharge to produce ozone.

5. Apparatus in accordance with claim 1, wherein the analytical apparatus is employed to measure oxides of nitrogen and has means for providing nitric oxide for reaction with the ozone in the reactor chamber.

6. In an analytical method in which ozone is generated in an ozone generator and in which the generated ozone reacts in a reactor chamber to produce chemiluminescence, the improvement comprising purifying the output of the ozone generator, and supplying the purified ozone to the reactor chamber.

7. A method in accordance with claim 6, wherein the purifying is accomplished by passing the output of the ozone generator through a bed of silica gel particles.

8. A method in accordance with claim 7, wherein the ozone is generated by an electric discharge.

9. A method in accordance with claim 8, wherein the analytical method is employed to measure oxides of nitrogen, and nitric oxide is reacted with the ozone in the reactor chamber.

10. A method of treating an output stream of an ozone generator, which comprises passing the output stream over silica gel to remove impurities from the ozone in the output stream.

11. A method in accordance with claim 10, wherein the ozone is generated by passing air through an electric discharge type ozone generator.

12. A method in accordance with claim 10, wherein the output stream is passed through a bed of particulate silica gel.

13. In an analytical method in which ozone is generated in an ozone generator and in which the generated ozone reacts in a reactor chamber to produce chemiluminescence, the improvement comprising increasing the accuracy of said analytical method by purifying the output of the ozone generator, and supplying the purified ozone to the reactor chamber.

* * * * *